(12) United States Patent
Simpson

(10) Patent No.: US 6,258,249 B1
(45) Date of Patent: Jul. 10, 2001

(54) STERILIZATION OF SURGICAL SITES

(75) Inventor: Charles Lee Simpson, Austin, TX (US)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/437,597

(22) Filed: Nov. 10, 1999

(51) Int. Cl.$^7$ .............................. B01D 17/06; C25F 1/00; A61B 18/04; A61D 1/10
(52) U.S. Cl. .................... 205/687; 205/692; 606/32; 606/122; 606/126
(58) Field of Search .................... 205/687, 692; 606/32; 607/122, 126

(56) References Cited

U.S. PATENT DOCUMENTS

| 4,419,248 | 12/1983 | Costerton | 210/764 |
|---|---|---|---|
| 4,542,169 | 9/1985 | Costerton | 523/121 |
| 4,800,959 | 1/1989 | Costerton et al. | 166/246 |
| 5,174,378 | 12/1992 | Costerton et al. | 166/246 |
| 5,312,813 | 5/1994 | Costerton et al. | 514/29 |
| 5,462,644 | * 10/1995 | Woodson | 204/131 |

FOREIGN PATENT DOCUMENTS 0 147 970 A1   10/1985   (EP) .

* cited by examiner

*Primary Examiner*—Edna Wong
(74) *Attorney, Agent, or Firm*—Timothy L. Scott

(57) ABSTRACT

A method for the treatment of an infected area within a body. The method comprises applying a electrically conductive biocide composition to an infected area within a body that has been exposed during surgery. Then, an electric field is applied to the biocide composition. The electric field strength and duration of application may be sufficient to produce killing of microorganisms in the infected area.

34 Claims, No Drawings

STERILIZATION OF SURGICAL SITES

BACKGROUND OF THE INVENTION

It has been reported that a biofilm is a conglomerate of microbial organisms embedded in a highly hydrated matrix of exopolymers, typically polysaccharides, and other macromolecules (see U.S. Pat. Nos. 5,312,813 and 5,462,644, and references cited therein). Biofilms may contain either single or multiple microbial species and readily adhere to such diverse surfaces as river rocks, soil, pipelines, teeth mucous membranes, and medical implants. By some estimates biofilm-associated cells outnumber planktonic cells of the same species by a ratio of 1000–10,000:1 in some environments.

Prevention of colonization by and eradication of biofilm-associated microorganisms is an important, and often difficult to solve, problem in medicine. Unlike planktonic organisms, which are relatively susceptible to biocides, e.g., antibiotics, the structural matrix established during biofilm formation can make the colonizing cells able to withstand normal treatment doses of a biocide. It is known that when organisms are isolated from biofilms and then grown in planktonic culture, they lose many of the characteristics associated with the progenitor cells, in particular the ability to produce a glycocalyx. In the biofilm, the glycocalyx matrix appears to serve as a barrier which protects and isolates the microorganisms from host defense mechanisms, such as antibodies and phagocytes, as well as from antimicrobial agents including surfactants, biocides and antibiotics. The aforementioned patents report that in one study, biofilm-associated bacteria were able to survive a concentration of antibiotic 20 times the concentration effective to eliminate the same species of bacteria grown in planktonic culture.

Biofilm infections can occur in a variety of disease conditions. In some tissue infections, such as prostatitis, the infective bacterium is capable of growing in the infected tissue in both biofilm (sessile) and circulating (planktonic) form. Although growth of the planktonic cells can be controlled by antibiotic treatment, the biofilm itself may be refractory to treatment, providing, in effect, a reservoir of infection which can lead to recurrence of the infection after antibiotic treatment.

Biofilm formation can also be a serious complication in bioimplants, such as bone prosthesis, heart valves, pacemakers and the like. Biofilm formation on exposed surface of a bioimplant can degrade the function of the implant, as in the case of implanted valves, lead to serious joint or bone infections, as in the case of a bone prosthesis, and in all cases, provide a source of difficult-to-treat septic infection. In the case of heart valve endocarditis cases a surgeon is forced to dissect all infected tissue, treat locally with antibiotics and antiseptics followed by valve replacement. Unfortunately, the treatment is often unsuccessful over time due to perivalvular leak caused by a continuing infection. If the surgeon had a more effective method of treating the infection during surgery, valve replacement outcomes could be improved.

While U.S. Pat. No. 5,312,813 discloses in vivo treatment of a urinary tract infection, for example, there is no mention of the treatment of an infection during the course of surgery. U.S. Pat. No. 5,462,644 is similar in this regard. In both these patents, in vivo treatment may instead be accomplished by administering a biocide orally with electrical current then being applied across the area to be treated. Thus, the in vivo treatment in these cases is accomplished by non-invasive means and outside of the context of surgery.

The present inventor has recognized that a need exists to enable surgeons to treat infected areas during surgery to thereby enhance probabilities for success of re-implant of a bio-prosthesis. The present invention provides a solution to one or more of the disadvantages and deficiencies described above.

SUMMARY OF THE INVENTION

The present invention provides a method of killing microorganisms in a biofilm within a human body that has been exposed during the course of surgery. In general, this method may be accomplished by surrounding the area to be treated that has been exposed to surgery with a composition containing a biocide and then providing an electrical current across the biocide composition. The biocide composition may be thickened or in the form of a gel.

In one broad respect, the invention comprises a method for the treatment of an infected area within a body, comprising applying an electrically conductive biocide composition to an infected area within a body that has been exposed during surgery, and applying an electric field to the biocide composition, wherein the electric field strength and duration of application are sufficient to produce killing of microorganisms in the infected area. In one embodiment, the source of electric field may be remote from the infection. That is, the infectious biofilm need not be in direct contact with the electrodes or source of the electric current. Preferable, the electric field strength and duration of application are sufficient to essentially eliminate the microorganisms of the infection or biofilm. As used herein, electrically conductive biocide composition refers to an aqueous composition typically containing an electrolyte, a buffer and one or more biocides. By biocides it is meant antibiotics, antiseptics, anti-fungal agents, disinfectants and sterilants. Alternatively, the biocide may be generated in situ upon application of an electric field to the electrically conductive medium.

The invention further provides a method for disinfecting or sterilizing devices infected with biofilms, wherein the device is implanted in a body, comprising applying an electrically conductive biocide composition to a device within a body that has been exposed during surgery, and applying an electric field to the biocide composition, wherein the electric field strength and duration of application are sufficient to produce killing of the microorganisms in the biofilm. In one embodiment, the biocides are present in a concentration which is less than effective to kill the biofilm microorganisms in the absence of the electric field. The electric field is preferably generated by currents between the electrodes of at least about 1 to about 200 milliamps, most preferably between about 1 and about 50 milliamps.

An alternative embodiment of this invention includes encapsulation of the surgical site between plates thereby creating a chamber which is filled with the electrically conductive biocide composition. An electrical current could then be applied to the plates, thereby providing current across the biocide composition.

DETAILED DESCRIPTION OF THE INVENTION

Representative biofilms and infections to be treated by the practice of this invention include the biofilms that are disclosed in U.S. Pat. Nos. 5,462,644 and 5,312,813, the contents of which are expressly incorporated herein by reference. In general, biofilms are composed of colonies of microorganisms, typically bacterial cells, but also colonies of yeast, fungi, mold or other colonizing microorganisms. The biofilm may be in the form of clumps or colonies of cells, which are anchored to a surface.

It has been stated in the literature that the cells in a biofilm are embedded in a hydrated matrix of exopolymers and other filamentous macromolecules, typically glycopeptides. The matrix formed by the filamentous material serves to anchor and coalesce the cells in the biofilm. The matrix, along with other cellular changes which occur on colonization, serves to protect colonized cells against biocidal agents to which the biofilm may be exposed.

The surface and infection/biofilm formed thereon are in contact with an aqueous medium, such as a body fluid, such as blood or lymph, which supplies the issue on which the biofilm is formed. The medium may carry planktonic cells onto he biofilm, where the cells may become incorporated in the biofilm; conversely, sessile cells in the biofilm may break off, individually or in clumps to form part of the circulating cell population.

In accordance with the present invention, a biocide composition is applied to the infected area. The biocide composition, which is electrically conductive, contains one or more biocides (either an added biocide or one generated in situ by an electric field).

The biocide included in the composition used in the practice of this invention is effective in killing the infecting microorganism. An appropriate biocide may be selected by testing a culture of the bacterial cells against a panel of biocides. Among the biocides which may be useful in the present invention are active chlorines such as, sodium hypochlorite, calcium hypochlorite, elemental chlorines, hypochlorous acid. Hypochlorite ion, and chlorine dioxides; quaternary ammonium compounds such as monoalkyltrimethyl ammonium salts, monoalkyldimethylbenzyl ammonium salt, dialkyldimethyl ammonium salts, heteroaromatic ammonium salts, polysubstituted quaternary ammonium salts, bis quaternary ammonium salts, and polymeric quaternary ammonium salts; compounds based on metals such as silver, cobalt, copper, iron. lead gold, silver, mercury, nickel, zinc, aluminum, tin, manganese, and platinum; peroxides such as hydrogen peroxide, peroxyacetic acid, peroxyheptanoic acid, peroxynonanoic acid, monoperglutaric acid, succinyl peroxides, and diperglutaric acid; and aldehydes such as glutaraldehyde, formaldehyde, glyoxal, malonaldehyde, succinaldehyde, and adipaldehyde. Among the antibiotics which are useful in the present invention are those in the penicillin, cephalosporin, aminoglycoside, tetracycline, sulfonamide, macrolide antibiotics, and quinoline antibiotic families. Preferred antibiotics also include imipenem, aztreonam, chloramphenicol, erythromycin, clindamycin, spectinomycin, vancomycin, and bacitracin. Among the preferred anti-fungal agents are the imidazole compounds, such as ketoconazole, and the polyene microlide antibiotic compounds, such as amphotericin B.

Biocide concentrations which themselves are relatively ineffective in killing biofilm microorganisms are usefully employed to kill biofilm bacteria when used in combination with an electric field. Bacterial, yeast, fungus and mold cell biofilms can be treated effectively. Electrolytically generated in situ biocides, as well as a variety of added biocide compounds, including compounds from different families of antibiotics, antifungal agents, sterilants and disinfectants are useful in the treatment method. The desired biocide concentration, whether added or electrolytically generated, is one which is ineffective in killing biofilm microorganisms when applied in the absence of an electric field. Typically, the concentrations of biocide in the composition is greater than or equal to about 1 ng/ml, preferably greater than or equal to about 1 microgram/ml; less than about 1 g/ml, preferably less than or equal to about 1 mg/ml.

The biocide composition may be an electrolyte solution which is comprised of strong electrolytes such as sodium and calcium, and is capable of conducting a current between 1 and 200 milliamps. Electrolyte solutions may have conductivities of between 2.2 and $8 \times 10^5$ ohms/cm.

The composition may also contain a component which causes thickening or gelling of the composition. Non-limiting examples of representative thickeners include cellulose ethers such as hydroxypropyl cellulose, ethyl cellulose, ethyl hydroxyethyl cellulose, methyl cellulose, and other alkyl or hydroxy alkyl cellulose; silica including colloidal silica; clays such as bentonite and montmorillonite starch; alumina including colloidal alumina; gum arabic, tragacanth; agar; sugar derivatives; high molecular weight polyethylene oxides; guar gum; xanthan gum; polyvinyl pyrrolidone and methyl vinyl ether/maleic anhydride copolymers. When a thickener is used, the amount of such thickener can vary depending on the desired level of thickening for the given application. In general, the amount of thickener employed is about 1 to about 4 percent by weight.

The biocide composition may be based on an electrolyte solution. The electrolyte solution is comprised of strong electrolytes such as sodium and calcium, and is capable of conducting a current between 1 and 200 milliamps. Preferred electrolyte solutions include well known buffer systems such as Clark and Lubs solutions, pH 1.0–2.2 (Bower and Bates, J. Res Natn. Bur. Stand. 55, 197 (1955)); glycine-HCl buffer solutions, pH 2.2–3.6 at 25° C. (Sorenson, BZ 21, 131 (1909); Gomori, Meth. Enzmol. 1, 141 (1955)); Clark and Lubs solutions, pH 2.2–4.0 (Bower and Bates, J. Res Natn. Bur. Stand. 55, 197 (1955)); citric acid-$Na_2HPO_4$ (McIlvaine) buffer solution, pH 2.6–7.6 (McIlvaine, JBC 49, 183 (1921)); citric acid-sodium citrate buffer solutions, pH 3.0–6.2; beta, beta-dimethylglutaric acid-NaOH buffer solutions, pH 3.2–7.6 (Stafford, Watson, and Rand, BBA 18, 318 (1955)); sodium acetate-acetic acid buffer solutions, pH 3.7–5.6; succinic acid-NaOH buffer solutions, pH 3.8–6.0 (Gomeri, Meth. Enzymol. 1, 141 (1955)); sodium cacodylate-HCL buffer solutions, pH 5.0–7.4 (Pumel, Bull. Soc. Chim. Biol. 30, 129 (1948)); $Na_2HPO_4$—$NaH_2PO_4$ buffer solutions, pH 5.8–8.0 (Gomeri and Sorensons, Meth. Enzmol. 1, 143 (1955)); Clark and Lubs solution, pH 8.0–10.2 (Bower and Bates, J. Res Natn. Bur. Stand. 55, 197 (1955)); borate buffer solutions, pH 8.1–9.0 (Bates and Bower, Analyt. Chem. 28, 1322 (1956)); and phosphate buffer solutions, pH 11.0–11.9 (Bates and Bower, Analyt. Chem. 28, 1322 (1956)). The electrolyte solution preferably contains disinfectants or sterilants, such as active chlorines, quaternary ammonium compounds, heavy metals, peroxides and aldehydes or other antiseptics.

According to an important feature of the invention, it has been discovered that a biofilm is substantially more susceptible to cell killing by a biocide (either an added biocide or one generated in situ by an electric field) when the biofilm is placed in an electrolyte medium through which an electric field is applied. The electric field is applied at a level effective to produce killing of biofilm cells at biocide concentrations which are several times lower than normal biofilm biocide concentrations. Advantageously, the electric field enhances the effects of added biocides and enables them to be effective in killing both planktonic and biofilm bacteria at concentrations much lower than is effective in the absence of an electric field.

Once the composition is applied to the area to be treated, a current is applied across the area by means of the electric field. After a selected treatment time, the current is turned off and the biocide composition may be removed. For example, the biocide composition may be removed through aspiration of the area.

The electric field may be generated by placing a voltage potential across a pair of electrodes, usually indicated by "+" and "−" electric polarity symbols. Ions in the biofilm and surrounding composition serve as current carriers between the two electrodes. The electric field is applied by a voltage source, which may supply a direct current (DC) source, such as a battery, or a conventional alternating current (AC) or pulsed voltage source. The voltage level is typically set to between 0.5–20 volts, preferably between 1–10 volts, and preferably under conditions effective to generate a current of at least about 1–50 milliamp or greater between the electrodes which form the electric field. The effectiveness of the electric field on biofilm destruction will depend on the strength of the electric field, which in turn depends on the voltage and distance between electrodes, the duration of field application, the concentration of biocide at the biofilm during application of the electric field, and fluctuations in the field. The electric field is applied until a desired reduction in infected area is achieved. The particular type of device employed to generate the electric field is not considered to be critical in the practice of this invention. A wide variety of devices which generate a electric field of appropriate voltage and amperage may be used in the practice of this invention. Representative, non-limiting examples of such devices are described in U.S. Pat. Nos. 5,312,813 and 5,462,644.

This invention may be practiced in the context of a wide variety of surgical procedures on and within a living body, including that of a human body. These procedures may be employed, for example, in the context of re-implantation of a bioprosthesis such as a heart valve or any artificial valves, knees, hips, orthopedics, vascular access sites, shunts and the like.

From the foregoing, the treatment method allows biofilm and infections, which are often difficult or impossible to treat by biocide treatment alone, to be effectively controlled or eliminated in situ during the course of a surgical procedure, by enhancing the biocide effect selectively in the region of biofilm growth. The electric field used for enhancing biocide effect is itself safe and generally easy to generate, either by direct connection to a voltage source, or by magnetic induction. The method is applicable to a wide range of biofilm infections involving both natural tissue surfaces or bio-implant surfaces.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as illustrative embodiments. Equivalent elements or materials may be substituted for those illustrated and described herein, and certain features of the invention may be utilized independently of the use of other features, all as would be apparent to one skilled in the art after having the benefit of this description of the invention.

What is claimed is:

1. A method for the treatment of an infected area within a body, comprising applying an electrically conductive biocide composition to an infected area within the body that has been exposed during surgery, and applying an electric field to the biocide composition, wherein the electric field strength and duration of application are sufficient to produce killing of microorganisms in the infected area.

2. The method of claim 1, wherein the source of the electric field is remote from the infectious area.

3. The method of claim 1, wherein biocide composition contains biocide in a concentration of about 1 ng/ml to about 1 g/ml.

4. The method of claim 1, wherein the infected area is composed of a biofilm that is composed predominately of bacteria, yeast or fungus.

5. The method of claim 1, wherein the biocide is an antibiotic selected from the family of antibiotics consisting of penicillins, cephalosporins, aminoglycosides, tetracyclines, sulfonamides, macrolide antibiotics and quinolones.

6. The method of claim 1, wherein the electrically conductive biocide composition is a buffered saline composition.

7. The method of claim 1, wherein the biocide composition includes a thickener.

8. The method of claim 1, wherein the electric field is substantially constant.

9. The method of claim 1, wherein the electrical field is a pulsed or alternating electric field.

10. The method of claim 1, wherein the electric field strength is generated by currents having a value in the range from about 1 to about 200 milliamps.

11. The method of claim 1, wherein said electric field is applied to the electrically conductive biocide composition for a period of time of between about 1 minute to about 48 hours.

12. The method of claim 1, wherein the biocide is present in the composition, in an amount which would be ineffective to completely kill the infected area if used in the absence of the electric field.

13. The method of claim 1 performed during the course of heart valve replacement surgery.

14. The method of claim 1, wherein the biocide is an antibiotic, an anti-fungal agent, a disinfectant, a sterilant, other antiseptic agents, hexachlorophene, cationic bisiguanides, iodine, iodophores, para-chloro-meta-xylenol, triclosan, furan preparations, methenamine, aldehydes, or alcohols.

15. The method of claim 14, wherein the cationic bisiguanides include chlorhexidene or cyclohexidene.

16. The method of claim 14, wherein iodine include povidone-iodine.

17. The method of claim 14, wherein iodophores include povidone-iodine.

18. The method of claim 14, wherein furan preparations include nitrofurantoin or nitrofurazone.

19. The method of claim 14, wherein aldehydes is in glute form.

20. The method of claim 1 wherein the biocide is sodium hypochlorite, calcium hypochlorite, elemental chlorine, hypochlorous acid, hypochlorite ion, a chlorine dioxide, a monoalkyltriethyl ammonium salt, a monoalkyldimethylbenzyl ammonium salt, a dialkyldimethyl ammonium salt, a heteroaromatic ammonium salt, a polysubstituted quaternary ammonium salt, a bis quaternary ammonium salt, a polymeric quaternary ammonium salt, a silver compound, a cobalt compound, a copper compound, an iron compound, a lead compound, a gold compound, a mercury compound, a nickel compound, a zinc compound, an aluminum compound, a tin compound, a manganese compound, hydrogen peroxide, peroxyacetic acid, peroxyhaptanoic acid, peroxynonanoic acid, monoperglutaric acid, succinyl peroxide, diperglutaric acid, glutaraldehyde, formaldehyde, glyoxal, malonaldehyde, succinaldehyde, adipaldehyde, a penicillin, a cephalosporin, an aminoglycoside, a tetracycline, a sulfonamide, a polyene macrolide, a quinoline, or an imidazole compound.

21. The method of claim 1, wherein the body is a human body.

22. A method for disinfecting or sterilizing an implanted device infected with a biofilm, comprising applying an electrically conductive biocide composition to a device within a body that has been exposed during surgery, and applying an electric field to the biocide composition, wherein the electric field strength and duration of application being sufficient to produce killing of the microorganisms in the biofilm.

23. The method of claim 22, wherein the device is a heart valve.

24. The method of claim 22 wherein the biocide is sodium hypochlorite, calcium hypochlorite, elemental chlorine, hypochlorous acid, hypochlorite ion, a chlorine dioxide, a monoalkyltrimethyl ammonium salt, a monoalkyldimethylbenzyl ammonium salt, a dialkyldimethyl ammonium salt, a heteroaromatic ammonium salt, a polysubstituted quaternary ammonium salt, a bis quaternary ammonium salt, a polymeric quaternary ammonium salt, a silver compound, a cobalt compound, a copper compound, an iron compound, a lead compound, a gold compound, a mercury compound, a nickel compound, a zinc compound, an aluminum compound, a tin compound, a manganese compound, hydrogen peroxide, peroxyacetic acid, peroxyhaptanoic acid, peroxynonanoic acid, monoperglutaric acid, succinyl peroxide, diperglutaric acid, glutaraldehyde, formaldehyde, glyoxal, malonaldehyde, succinaldehyde, adipaldehyde, a penicillin, a cephalosporin, an aminoglycoside, a tetracycline, a sulfonamide, a polyene macrolide, a quinoline, or an imidazole compound.

25. The method of claim 22, wherein the electric field strength is generated by currents having a value in the range from about 1 to about 200 milliamps.

26. The method of claim 22, wherein said electric field is applied to the electrically conductive biocide composition for a period of time of between about 1 minute to about 48 hours.

27. The method of claim 22, wherein the electrically conductive biocide composition is a buffered saline composition.

28. The method of claim 22, wherein the biocide composition includes a thickener or a gelling agent.

29. The method of claim 22, wherein the electric field is substantially constant.

30. The method of claim 22, wherein the electrical field is a pulsed or alternating electric field.

31. The method of claim 22, wherein the source of electric field is remote from the infectious area.

32. The method of claim 22, wherein biocide composition contains biocide in a concentration of about 1 ng/ml to about 1 g/ml.

33. A method for the treatment of an infected area within a body comprising:

applying an electrically conductive biocide composition with a thickener to an infected area within the body that has been exposed during surgery; and applying an electric field to the biocide composition, wherein the electric field strength and duration of application are sufficient to produce killing of microorganisms in the infected area.

34. A method for disinfecting or sterilizing an implanted device infected with a biofilm comprising:

applying an electrically conductive biocide composition with a thickener to a device within a body that is exposed during surgery; and applying an electric field to the biocide composition with the thickener, wherein the electric field strength and duration of application being sufficient to produce killing of the microorganisms in the biofilm.

* * * * *